(12) United States Patent
Le Gouellec et al.

(10) Patent No.: US 9,556,442 B2
(45) Date of Patent: Jan. 31, 2017

(54) ATTENUATED AND ADAPTED STRAIN OF PSEUDOMONAS FOR DELIVERING ANTIGENS

(71) Applicants: UNIVERSITE JOSEPH FOURIER-GRENOBLE 1, St. Martin d'Hères (FR); CENTRE HOSPITALIER UNIVERSITAIRE GRENOBLE, La Tronche (FR)

(72) Inventors: Audrey Le Gouellec, Uriage (FR); Bertrand Toussaint, Saint Egreve (FR); Benoît Polack, Saint Martin le Vinoux (FR)

(73) Assignees: UNIVERSITE GRENOBLE ALPES, Saint Martin d'Hères (FR); CENTRE HOSPITALIER UNIVERSITAIRE GRENOBLE, La Tronche (FR)

( * ) Notice: Subject to any disclaimer, the term of this patent is extended or adjusted under 35 U.S.C. 154(b) by 6 days.

(21) Appl. No.: 14/364,322

(22) PCT Filed: Dec. 12, 2012

(86) PCT No.: PCT/EP2012/075167
§ 371 (c)(1),
(2) Date: Jun. 11, 2014

(87) PCT Pub. No.: WO2013/087667
PCT Pub. Date: Jun. 20, 2013

(65) Prior Publication Data
US 2014/0335125 A1  Nov. 13, 2014

(51) Int. Cl.
*A01N 63/00*  (2006.01)
*A01N 65/00*  (2009.01)
(Continued)

(52) U.S. Cl.
CPC .......... *C12N 15/78* (2013.01); *A61K 39/0011* (2013.01); *C07K 14/435* (2013.01); *C12N 1/20* (2013.01);
(Continued)

(58) Field of Classification Search
CPC .................... A61K 2039/52; A61K 2039/522; C12N 1/00; C12N 1/20; C12N 1/36
See application file for complete search history.

(56) References Cited

U.S. PATENT DOCUMENTS 7,939,319 B2   5/2011  Polack et al.

OTHER PUBLICATIONS

Epaulard et al., (Clin Vaccine Immunol. Feb. 2008.15(2):308-313. Published online Dec. 19, 2007).*
(Continued)

*Primary Examiner* — Ja'na Hines
(74) *Attorney, Agent, or Firm* — Harness, Dickey & Pierce, P.L.C.

(57) ABSTRACT

A process for obtaining an adapted strain of *Pseudomonas* includes the following steps: deleting the genes ExoS, ExoT, aroA and IasI in an initial *Pseudomonas* strain cultivated in a LB medium; progressively cultivating this strain in a chemically defined medium based on a glucose minimal medium supplemented with magnesium and calcium; wherein the adapted strain presents the same toxicity and secretion capacities than the initial strain, and its doubling time when cultivated in the chemically defined medium is less than 60 minutes. An adapted strain is furthermore treated to become 'killed but metabolically active'.

6 Claims, 5 Drawing Sheets

(51) Int. Cl.
*C12N 1/00* (2006.01)
*C12N 15/78* (2006.01)
*C12R 1/38* (2006.01)
*C12N 1/20* (2006.01)
*C12N 1/36* (2006.01)
*C07K 14/435* (2006.01)
*A61K 39/00* (2006.01)

(52) U.S. Cl.
CPC . *C12N 1/36* (2013.01); *C12R 1/38* (2013.01); *A61K 2039/522* (2013.01); *A61K 2039/523* (2013.01)

(56) References Cited

OTHER PUBLICATIONS

Epaulard, O., et al.; "Optimization of a type III secretion system-based *Pseudomonas aeruginosa* live vector for antigen delivery;" Clinical and Vaccine Immunol., vol. 15, No. 2, Feb. 2008; pp. 308-313.
Brockstedt, D. G., et al.; "Killed but metabolically active microbes: a new vaccine paradigm for eliciting effector T-cell responses and protective immunity;" Nat. Med., vol. 11, No. 8, Aug. 2005; pp. 853-860.
Epaulard, O. T., et al.; "Anti-tumor immunotherapy via antigen delivery from a live attenuated genetically engineered *Pseudomonas aeruginosa* type III secretion system-based vector;" Mol. Ther., vol. 14, No. 5, Nov. 2006; pp. 656-661.
Wollowitz, S.; "Fundamentals of the psoralen-based Helinx technology for inactivation of infectious pathogens and leukocytes in platelets and plasma;" Seminars in Hematol., vol. 38, No. 4, Supp. 11, Oct. 2001; pp. 4-11.
DeBell, R. M.; "Production of exotoxin A by *Pseudomonas aeruginosa* in a chemically defined medium;" Infection and Immun., vol. 24, No. 1, Apr. 1979; pp. 132-138.
Buonaguro, L., et al.; "Translating tumor antigens into cancer vaccines;" Clinical and Vaccine Immunol., Minreview, vol. 18, No. 1, Jan. 2011; pp. 23-34.
Novellino, L., et al.; "A listing of human tumor antigens recognized by T cells: Mar. 2004 update;" Cancer Immunol Immunother, 54(3), Mar. 2005; pp. 187-207.
Derouazi, M., et al.; "Optimal epitope composition after antigen screening using a live bacterial delivery vector: application to TRP-2;" Bioeng. Bugs, 1 (1), Jan.-Feb. 2010; pp. 51-60.
Dacheux, D., et al.; "Cell death of human polymorphonuclear neutrophils induced by a *Pseudomonas aeruginosa* cystic fibrosis isolate requires a functional type III secretion system;" Infection and Immun., vol. 67, No. 11, Nov. 1999; pp. 6164-6167.
Papezova, K., et al.; "Ordered expression of virulence genes in *Salmonella enterica* serovar typhimurium;" Folia Microbiologica, Praque, CZ, vol. 52, No. 2, Jan. 1, 2007, XP002587756; pp. 107-114.
Harcombe, W. R., et al.; "Impact of phages on two-species bacterial communities;" Applied and Environmental Microbiology, vol. 71, No. 9, Sep. 2005, XP002676592; pp. 5254-5259.
Martin, C. H., et al., "High-titer production of monomeric hydroxyvalerates from levulinic acid in *Pseudomonas putida*;" Journal of Biotechnology, Elsevier Science Publishers, Amsterdam, NL, vol. 139, No. 1, Jan. 1, 2009, XP025796274; pp. 61-67.
Chan, R., et al.; "Influence of culture conditions on expression of the mucoid mode of growth of *Pseudomonas-aeruginosa*;" Journal of Clinical Microbiology, vol. 19, No. 1, Jan. 1984, XP002676593; pp. 8-16.
Blumentals, I. I., et al.; "Development of a defined medium and two-step culturing method for improved exotoxin a yields from Pseudomonas-aeruginosa ", Applied and Environmental Microbiology, vol. 53, No. 9, Sep. 1987, XP002676594; pp. 2013-2020.
Lankowski, A. J., et al.; "Killed but metabolically active *Salmonella typhimurium*: application of a newtechology to an old vector;" Journal of Infectious Diseases, University of Chicago Press, Chicago, Illinois , vol. 195, No. 8, Apr. 1, 2002, XP009099076; pp. 1202-1211.
Skoberne, M., et al.; "KBMA *Listeria monocytogenes* is an effective vector for DC-mediated induction of antitumor immunity;" Journal of Clinical Investigation, vol. 118, No. 12, Dec. 2008, XP002676595; 12 pages.
Skoble, J., et al.; "Killed but metabolically active *Bacillus anthracis* vaccines induce broad and protective immunity against anthrax;" Infection and Immunity, vol. 77, No. 4, Apr. 2009, XP002676596; pp. 1649-1663.
Wang, Y., et al.; "Optimization of antitumor immunotherapy mediated by type III secretion system-Based live attenuated bacterial vectors;" Journal of Immunotherapy, vol. 35, No. 3, Apr. 1, 2012, XP009159387; pp. 223-234.

* cited by examiner

- popB: 40KD
- popD: 31KD
- P-OVA: 21.7KD

ATTENUATED AND ADAPTED STRAIN OF PSEUDOMONAS FOR DELIVERING ANTIGENS

CROSS-REFERENCE TO RELATED APPLICATIONS

This application is a National Phase Entry of International Application No. PCT/EP2012/075167, filed on Dec. 12, 2012, which claims priority to European Patent Application No. 11306636.9, filed on Dec. 12, 2011, both of which are incorporated by reference herein.

FIELD

The present invention concerns a method for obtaining an attenuated and adapted strain of *Pseudomonas* for its use in human vaccines. The invention also concerns the obtained strain, and the other treatments useful to improve the safety of the *Pseudomonas* strain, without decreasing its immunogenicity.

BACKGROUND

Bacteria have been developed for use as vaccines that deliver heterologous antigens. These bacteria have been modified to contain nucleic acid sequences encoding a protein or antigen of interest. However, injection of native virulent infectious bacteria is potentially deleterious to the recipient organism. Therefore, virulence of bacteria has to be attenuated before their use in immunotherapy.

Due to the endowed effective ability to deliver antigen to antigen presenting cells in vivo, type III secretion system (T3SS or TTSS) based attenuated bacterial vectors attracted more and more attention for their potential use, in particular for cancer vaccine development. In the last decades, the use of Gram-negative bacteria, such as *Salmonella, Shigella, Yersinia* and *Pseudomonas* which use their powerful secretion machinery—type III secretion system to deliver bacterial effectors to the membrane or into the host cell cytoplasm, has attracted more and more attention for their potential use for cancer vaccine development (Epaulard et al., 2006). Until now, T3SS based bacteria has been proved as a carrier for cancer vaccines which provide the protection against several tumor models like glioma, prostate cancer, breast cancer and fibrosarcoma in mice.

Beside their high efficiency, the safety of bacterial vectors are very important for clinical application. In our previous work described in the article from Epaulard et al., published in 2008, two attenuated strains of *Pseudomonas* were described:
  one attenuated strain "CHA-OST", in which the exoS exoT genes encoding two major T3S toxin exoenzymes—ExoS and ExoT—have been deleted, demonstrated efficient antigen delivery ability and tumor protection performance;
  a more attenuated strain "CHA-OAL", in which beside exoS and exoT genes, the aroA and IasI genes have also been deleted. The aroA gene encodes the 3-phosphoshikimate 1-carboxyvinyltransferase which is a key enzyme in aromatic amino acid synthesis and the IasI gene encodes the enzyme which produces quorum sensing (QS) homoserine lactones 3-oxo-C12-HSL.
This second strain CHA-OAL has a greatly reduced toxicity while keeping a good efficiency at high doses. This maximally attenuated strain may represent the best compromise between virulence attenuation and efficiency so that it was endowed the potential for clinical applications.

The patent EP 1 692 162 describes an expression vector of chimeric proteins, comprising the functional part of the proteins ExoS or ExoT from *Pseudomonas aeruginosa*, and an antigen of interest. The chimeric protein can be expressed by a strain transformed with said vector, and be "injected" into the cytoplasm of an antigen-presenting cell via the TTSS system. Preferentially, the transformed strain is a CHA-OST strain wherein the genes exoS and exoT have been deleted.

Recently, a new concept of vaccines that are "killed but metabolically active" (KBMA) have been described. They retain the immunological properties of live organisms but have a safety profile closer to that of killed organisms. Initially, the KBMA vaccine strategy was demonstrated by Brockstedt et al. with *Listeria monocytogenes* bacteria (Brockstedt et al., 2005). The deletion of two uvr genes (A and B) coding for exonucleotidase A and B subunit renders bacteria sensitive to psoralen-induced crosslink by exposure to long wavelength UVA light (Wollowitz, 2001). However, it is unclear whether this photochemical treatment could be applied to *Pseudomonas* bacteria and whether the type III secretion system would work after this treatment.

For clinical purpose, it is also important to join good manufacturing practices for vaccine production. In particular, bacterial vectors should be produced in chemically defined medium with constant growth performance to ensure the quality of the product.

Indeed, one of the main technical problem met with the culture of attenuated *Pseudomonas* strains is their poor growth rate in standard chemically defined growth media. In recent studies, one chemically defined medium—glucose minimal (M9) medium has been applied in different bacterial species culture, such as *E. coli, Salmonella Typhimurium, Pseudomonas putida*, for the investigations of genes expression, protein expression and bacterial communities. This medium was previously developed by DeBell R M and had been proved to be ideal for Exotoxin A production by *P. aeruginosa* (DeBell, 1979).

There is a need in the art for an optimized chemically defined medium, allowing a high and constant growth rate for *Pseudomonas* attenuated strains. Preferentially, these strains are transformed with a vector of expression such as described in patent EP 1 692 162.

SUMMARY

The present invention is related to a process for obtaining an adapted strain of *Pseudomonas*, comprising the following steps:
  Deleting the genes ExoS, ExoT, aroA and IasI in an initial *Pseudomonas* strain cultivated in a LB medium,
  Progressively cultivating this strain in a chemically defined medium based on a glucose minimal medium (M9) supplemented with magnesium and calcium,
wherein the adapted strain presents the same toxicity and secretion capacities than the initial strain, and its doubling time when cultivated in said chemically defined medium is less than 60 minutes.

In a preferred aspect of the invention, the *Pseudomonas* strain is furthermore treated with the KBMA process to become "killed but metabolically active". The invention is also related to a "killed but metabolically active" *Pseudomonas* strain. The present invention is also related to a *Pseudomonas* strain, such as obtained by the process previously described, characterized by a better growth in the chemically defined medium than in LB medium, with a similar toxicity and a similar activity of the T3SS injection system than the strain before adaptation.

According to the present invention, the attenuated adapted *Pseudomonas* strain expresses a chimeric protein composed of the N-terminal sequence of ExoS or ExoT, and an antigen of interest. The invention is also related to immunogenic compositions and vaccines comprising the previously described strains. Finally, the invention also concerns a vaccination strategy characterized by multi-position injections of the attenuated and adapted strain of *Pseudomonas*, to the organism.

DETAILED DESCRIPTION

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Sambrook et al., 2001. Conventional immunological techniques are explained in Current protocol in Immunology, Coligan, John Wiley & Sons (2005).

It must be noted that as used herein and in the appended claims, the singular forms "a", "an", and "the" include plural reference unless the context clearly dictates otherwise. Thus, for example, a reference to "a strain" includes a plurality of such strains, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The present invention is related to a process for obtaining an adapted strain of *Pseudomonas*, comprising the following steps:
  Deleting the genes ExoS, ExoT, aroA and IasI in an initial *Pseudomonas* strain cultivated in a LB medium,
  Progressively changing the culture medium from LB medium to a chemically defined medium comprising magnesium and calcium, and
  Selecting the adapted strains presenting a doubling time inferior to 60 minutes when cultivated in said chemically defined medium.
Advantageously, the adapted strain presents the same toxicity and secretion capacities than the initial strain.

As used herein, the following terms may be used for interpretation of the claims and specification. In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "*Pseudomonas*" designates a genus of gammaproteobacteria, belonging to the family Pseudomonadaceae containing 191 validly described species. All species and strains of *Pseudomonas* are Gram-negative rods, and are classified as strict aerobes. Among them, *Pseudomonas aeruginosa* is a highly relevant opportunistic human pathogen.

Gram-negative bacteria use different types of secretion systems for their own purposes. In particular, the type III secretion system (T3SS) is involved in the cytotoxicity of *Pseudomonas* strains.

The first step of the process according to the invention is the deletion of the genes ExoS, ExoT, aroA and IasI in an initial *Pseudomonas* strain cultivated in a LB medium. The exoS and exoT genes encodes two major T3S toxin exoenzymes—ExoS and ExoT. The aroA gene encodes the 3-phosphoshikimate 1-carboxyvinyltransferase which is a key enzyme in aromatic amino acid synthesis and the IasI gene encodes the enzyme which produces quorum sensing (QS) homoserine lactones 3-oxo-C12-HSL. As previously described in (Epaulard et al., 2008), the obtained strain present an attenuation of its virulence while keeping a good efficiency to induce an immunogenic response, when administered to an organism.

Luria Bertani (LB), a nutritionally rich medium, is primarily used for the growth of bacteria. The LB medium is widely used as a growth medium for all types of bacteria, and its composition is well known by the man skilled in the art.

The second step of the process according to the invention is a progressive change of growth medium, from LB medium to a chemically defined medium based on a glucose minimal medium (M9) supplemented with magnesium and calcium, named MM9 medium. Advantageously, the replacement of LB broth by the MM9 medium was made according to the following proportions: 100% LB→50% LB-MM9→20% LB-MM9→5% LB-MM9→2% LB-MM9→100% MM9. For each step, at least two days of adaptation were realized, until that the adapted strain proliferates stably in 100% MM9 medium.

The third step of the process according to the invention is the selection of adapted strains, characterized by a growth capacity defined by a "doubling time" than is less than 60 minutes. The "doubling time" is the necessary period for a bacterial colony to double its population when cultivated in optimal conditions (37° C. in a medium growth, under constant moving).

The final product of the process according to the invention is an "adapted strain" presenting the following features: the adapted strain presents the same toxicity and secretion capacities than the initial strain, while its doubling time when cultivated in said chemically defined medium is less than 60 minutes. Advantageously, its doubling time in said chemically defined medium is less than 50 minutes, and more preferentially is less than 45 minutes.

In a specific aspect of the invention, the MM9 medium is a M9 medium supplemented with 1 mM $Mg^{2+}$ and 1 mM $Ca^{2+}$. Advantageously, the chemically defined medium MM9 has the following composition:

TABLE 1

Composition of modified M9 (MM9) medium

| | | |
|---|---|---|
| Extract of synthetic yeast | 4 g/L | |
| Tryptophan | 1 mmol/L | (0.2 g/L) |
| Glucose | 14 mmol/L | (2.5 g/L) |

TABLE 1-continued

Composition of modified M9 (MM9) medium

| Glycerol | 1% | |
|---|---|---|
| FeSO4 | 0.4 g/L | |
| Citric acid | 2 mmol/L | (0.36 g/L) |

M9 Salts Medium 5X (Sigma) approximate composition per liter

| Na2PO3 anhydre | 33.9 g | |
|---|---|---|
| KPO3 | 15.0 g | |
| NaCl | 2.5 g | |
| NH4Cl | 5.0 g | |
| MgSO$_4$ | 1 mmol/L | (50 mg/L) |
| CaSo$_4$ | 1 mmol/L | (50 mg/L) |
| Eau | qsp 1 L | |

In a specific aspect of the invention, the adapted strain is furthermore treated to become "killed but metabolically active". The process to obtain killed but metabolically active bacteria can be summarized as follow:

A *Pseudomonas* strain is deleted for the gene uvrAB; any technique known by the man skilled in the art can be used to obtain this deletion;

A photochemical inactivation with UVA is performed in presence of S-59 psoralen;

Toxicity, antigen production and antigen secretion via the TTSS system by the treated strain are assessed.

For more details on the KBMA process, see (Brockstedt et al., 2005) and (Wollowitz, 2001), herein incorporated by reference. In a preferred aspect of the invention, the obtention of a KBMA *P. aeruginosa* strain is made in presence of a concentration of 10 µM of S59-psoralen with an UVA irradiation at a dose of 7.2 J/cm$^2$.

The invention is also related to a process such as described above, to obtain a Killed But Metabolically Active *Pseudomonas* strain, and to the obtained strain. In particular, the KBMA process can be applied to a "CHA-OST" or to a "CHA-OAL" strain. The invention is also related to a KBMA *Pseudomonas* strain, non-toxigenic and less virulent than the initial non-treated strain, while keeping T3SS secretion capacities. In a specific aspect of the invention, the *Pseudomonas* strain has been attenuated prior the KBMA treatment, by the deletion of the genes exoS and exoT.

In another aspect of the invention, the *Pseudomonas* strain has been attenuated prior the KBMA treatment, by the deletion of the genes exoS, exoT, aroA and IasI. In another aspect of the invention, the *Pseudomonas* strain has been adapted on a MM9 medium prior the KBMA treatment. In another aspect of the invention, the *Pseudomonas* strain has been attenuated by the deletion of the genes exoS, exoT, aroA and IasI and adapted on a MM9 medium, prior the KBMA treatment.

The invention is also related to a *Pseudomonas* strain such as obtained by anyone of the processes described above, wherein the adapted strain presents the same toxicity and secretion capacities than the initial strain, and its doubling time when cultivated in said chemically defined medium is less than 60 minutes. In a particular embodiment of the invention, the strain expresses a chimeric protein composed of the N-terminal sequence of ExoS or ExoT, and an antigen of interest. Such strain was previously described in the patent EP 1 692 162, which is incorporated herein by reference.

In a preferred aspect of the invention, the strain belongs to the species *Pseudomonas aeruginosa*. The invention is also related to a specific adapted strain of *Pseudomonas* that has been deposited at the National Collection of Microorganisms Cultures (CNCM), Pasteur Institute (25 rue du Docteur Roux, 75724 Paris) on Dec. 1, 2011 under the accession number CNCM I-4564. The invention is also related to an immunogenic composition comprising one of the adapted strain of *Pseudomonas* such as described above.

The invention is also related to a vaccine comprising the immunogenic composition comprising one of the adapted strain of *Pseudomonas* such as described above and a pharmaceutically acceptable carrier or adjuvant. The man skilled in the art knows the best adjuvant for each vaccine composition.

The present invention is also related to a method of inducing an immune response in a host comprising administering to the host by injections in multiple positions an effective amount of the vaccine such as described above. In a particular aspect of the invention, the method of inducing an immune response is based on a vaccination protocol comprising four subcutaneous injections in right and left flanks of a sufficient amount of the vaccine such as described above (see examples for more details).

The therapeutic use of the adapted and/or KBMA strain of the invention depends on the antigen being expressed by the strain. Indeed, the immune response shall be induced against a specific pathogen or tumor. Depending on the disease that has to be treated, a specific antigen of interest will be chosen to be expressed as a fusion protein by the *Pseudomonas* strain according to the invention. In a specific aspect of the invention, the antigen of interest is a tumoral or a viral antigen. In particular said antigen can be chosen among the list of: BAGE, CAMEL, CEA, DAM, GAGE, HER-2/neu, MAGE, MUM, MART, PSA, PSMA, RAGE, SAGE, and WT1. Preferentially, the antigen is chosen among the tumoral antigens listed in (Novellino et al., 2005) and (Buonaguro et al., 2011). Finally, the invention is also related to the use of an adapted strain of *Pseudomonas* such as described above, for preparing a vaccine composition.

EXAMPLES

Figure 1:
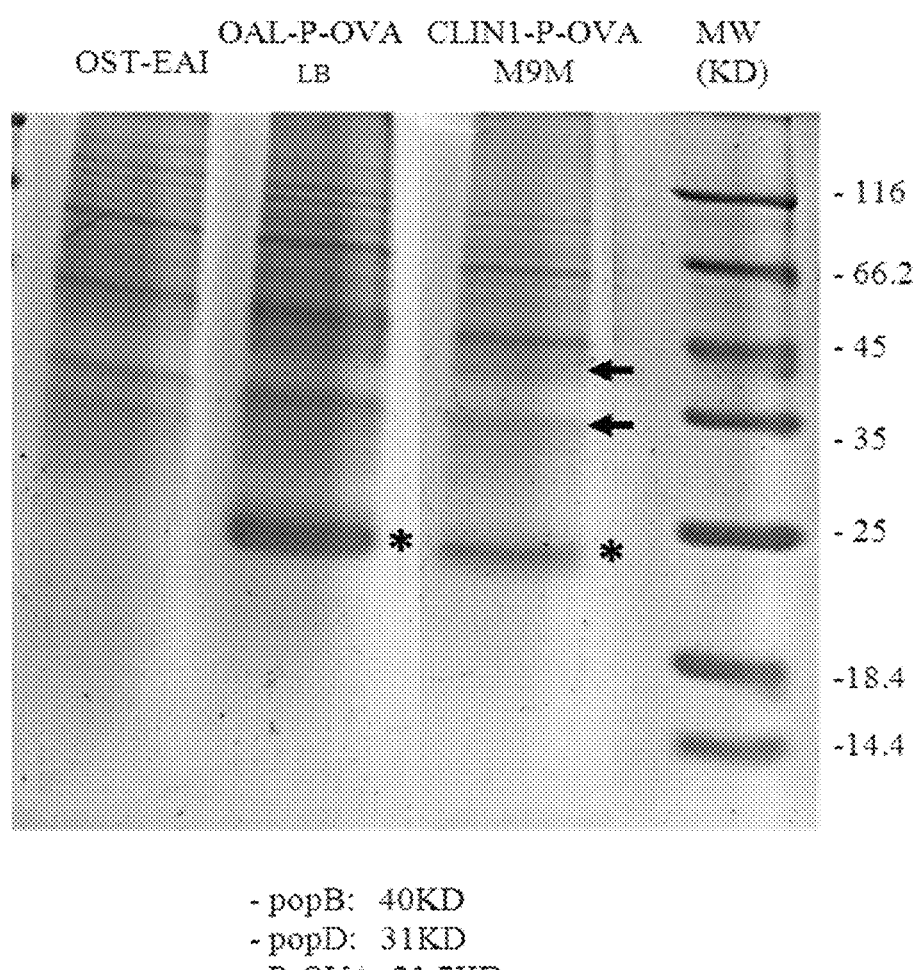
FIG. 1: Evaluation of T3SS-mediated fusion protein secretion by MM9 cultivated CHA-CLIN1 strain. The positions of popB (top arrow) and popD (bottom arrow) are marked with arrows; the positions of S54-PADRE-antigen fusion proteins are marked with stars.

Before describing the present invention in detail, it is to be understood that this invention is not limited to particularly exemplified methods and may, of course, vary.

Example 1

Adaptation of an Attenuated *Pseudomonas* Strain "CHA-OAL" Cultivated in LB Medium, into a Chemically Defined Medium (MM9)

We firstly adapted CHA-OAL strain in Debell M R modified M9 medium which was ideal for Pseudomenas ExoA protein production, but the growth rate of bacteria was not high enough. We further modified M9 medium by supplementing it with Mg2+ and Ca2+ and the composition of the modified M9 medium (MM9) is shown in table 1. In order to adapt the CHA-OAL strain in this medium, the replacement of LB by MM9 for CHA-OAL strain culture was progressive. At the end CHA-OAL strain stably proliferated in MM9 medium and the growth was much better than it was cultivated in LB broth (table 2).

TABLE 2

Growth kinetic (doubling time) of mutants CHA-OAL in LB and in MM9 broths after adaptation

| Mutant | Mean doubling time (min) during exponential growth | |
|---|---|---|
| | LB broth | MM9 broth |
| CHA-OAL | 88 | 43 |

This new strain adapted for growing in MM9 medium, with a doubling time of 43 minutes, was named CHA-CLIN1, and was deposited at the CNCM under accession number I-4564.

Example 2

Toxicity and Secretion Capacities of the Adapted Strain CHA-CLIN1 Obtained in Example 1

2.1. Toxicity: In order to verify if the adaption and the new growth conditions have modified the toxicity of CHA-CLIN1 strain, we assessed the in vivo toxicity of CHA-CLIN1 strain cultivated in LB or MM9 medium by observing mortality after one subcutaneous injection of $10^7$, $10^8$, or $10^9$ bacteria to 6-week-old female C57BL/6 mice. The toxicity of the new CHA-CLIN1 strain was compared with the toxicity of CHA-OST and CHA-OAL strains, previously described (table 3).

TABLE 3

In vivo toxicity test of CHA-OST and CHA-CLIN1 mutants

| Mutant | Dose | Mortality |
|---|---|---|
| CHA-OST (in LB) | $10^5$ | 0/6 |
| | $10^6$ | 0/6 |
| | $10^7$ | 4/6 |
| CHA-OAL (in LB) | $10^7$ | 0/6 |
| | $10^8$ | 0/6 |
| | $10^9$ | 0/6 |
| CHA-CLIN1 (in MM9) | $10^7$ | 0/6 |
| | $10^8$ | 0/6 |
| | $10^9$ | 0/6 |

It can be observed that the toxicity of CHA-CLIN1 strain in MM9 is very low compared to the toxicity of CHA-OST strain, and is the same than the toxicity of CHA-OAL strain, cultivated in LB medium.

2.2. Capacity of protein Secretion by TTSS: We tested if T3SS characters of CHA-CLIN1 strain were modified by both adaptation and growth in MM9 medium, compared to a non-adaptated strain grown in LB. We transformed CHA-OAL and CHA-CLIN1 strains with pEAI-S54-PADRE-OVACter (transformed strains are OAL-P-OVA and CLIN1-P-OVA, respectively) and assessed the secretion of the fusion protein in LB and MM9 medium.

Bacterial cultures for OST-EI (negative control strain), OAL-P-OVA and CLIN1-P-OVA strains were realized at 37° C. with shaking at 250 rpm. After an overnight pre-culture in LB containing 300 µg/mL carbenicillin, the bacteria were resuspended at 0.2, $OD_{600}$ in LB containing 300 µg/mL carbenicillin, 0.5 mM IPTG, 5 mM EGTA and 20 mM $MgCl_2$ until the $OD_{600}$ reaches a value between 1.5 and 2. Then, bacterial cultures were centrifuged at 17000 g for 15 min and the supernatant was recovered. For precipitation of proteins, perchloric acid was added to supernatant at a final concentration of 15% and incubated at 4° C., overnight. The next day, precipitated proteins were centrifuged at 17000 g, 4° C. for 30 min; proteins were washed two times with acetone (17000 g, 15 min), dried at room temperature and resuspended in 60 µL denaturation buffer (Tris HCL, dithiothreitiol, SDS, bromophenol blue, glycerol).

Then, proteins were analyzed by SDS-PAGE, in a 15% polyacrylamide gel (Ready Gels Recast Gel (Biorad®)), under 120 V, in Tris Glycine SDS migration buffer (Biorad®), and visualized by Coomassie Blue staining. The secretion results of the different strains are shown in FIG. 1. In this figure, the first lane presents strain OST-EAI which is the control strain that contains no antigen coding sequence. Three proteins are visualized:

PopB and PopD (marked with arrows), two structural proteins of T3SS that form the translocation channel: their presence is a positive control of a correct activation of T3SS;

the fusion protein P-OVA (marked with stars), observed for the transformed strains expressing the antigen cultivated both in LB medium and adapted in M9M medium.

Therefore, the TTSS secretion capacities of CHA-CLIN1 strain in MM9 are the same than the capacities of CHA-OAL strain cultivated in LB medium, after transformation with a plasmid pEAI-S54-PADRE-OVACter.

Example 3

Attenuation of a Strain "CHA-OST" by the KBMA Process

The nucleotide excision repair mutants OSTΔuvrAB (OS-TAB) were generated from the *P. aeruginosa* strain CHA- OST by Cre/lox-based mutagenesis {Quenee, 2005 #48} and sacB-based negative selection system. S59 psoralen/UVA inactivation of bacteria and viability assay. We determined the relative sensitivity to photochemical inactivation of OSTAB strain and its parental strain OST over a range of S-59 psoralen concentrations and an UVA dose of 7.2 J/cm2, using conditions established previously for gram negative bacteria {Lankowski, 2007 #162}.

Figure 2:
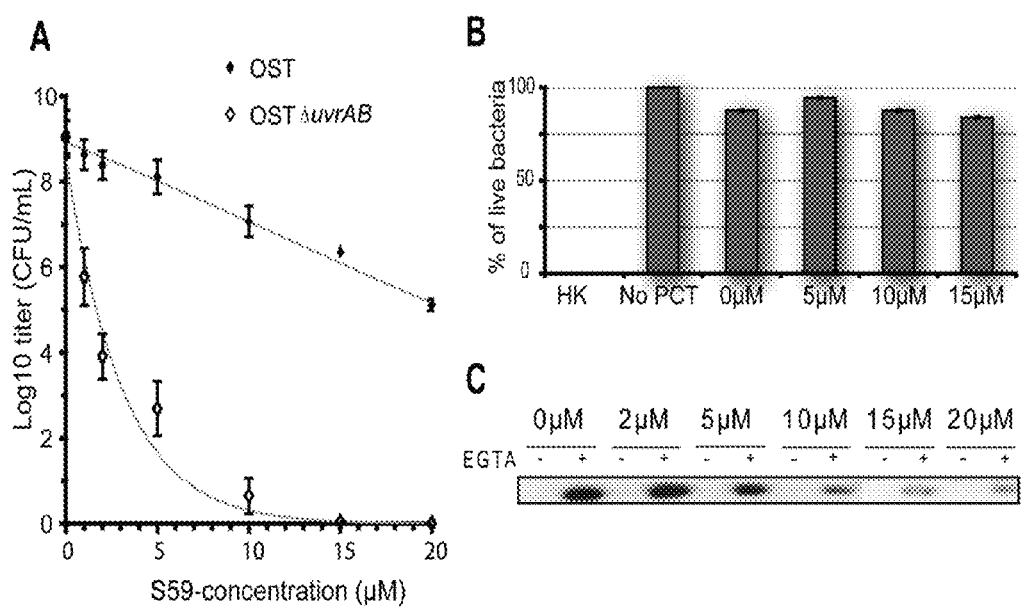
FIG. 2: Photochemically treated *P. aeruginosa* ΔuvrAB mutant is "killed but metabollically active". A. Viability of OST(wt) and OSTAB after treatment with the indicated S59 concentration based on colony forming unit on nutrient agar. Mean of 5 experiments realized in duplicates analyze with graphpad software. B. Analysis of *P. aeruginosa* viability after different treatment by Live/Dead BacLight staining kit (Molecular probe) and measurement of fluorescence in microplate reader. C. Detection by western blot of ExoS54-OVA in supernatant of *P. aeruginosa* photochemically treated with different level of amotosalen.

For photochemical treatment (PCT), the OSTΔuvrAB strain was cultivated in LB medium at 37° C. until $OD_{600}$ of 0.5. Different concentrations of S-59 psoralen were added and cultures were grown for an additional hour. 1 ml of culture per well ($OD_{600}$ of 1) was then transferred in 6-wells culture plate for UVA irradiation at a dose of 7.2 $J/cm^2$ in a Stratalinker 1800 device (Stratagen). Viability of photochemically inactivated cultures was assessed by serial dilution and plating on PIA for colony forming units. Points represent mean values of triplicates plates counted at the most appropriate dilution (FIG. 2A).

As expected, the OSTΔuvrAB strain was much more sensitive to PCT than OST. With 10 µM S-59 there was ~1 live replicating organism/$1.25 \times 10^8$ bacteria exposed for OSTAB, and $2.5 \times 10^6$ live bacteria for OST. Based on the Live/Dead BacLight Bacterial Viability kit (Molecular Probes), we then looked for the membrane integrity of the photochemical treated P. aeruginosa strain (FIG. 2B). Under the photochemical treatment, bacteria are unable to reproduce in nutrient medium but have intact membranes yet these may be scored as "alive". Therefore, the present example show that Pseudomonas strains can be subjected to the KBMA treatment, and become "killed but metabolically active", with intact membranes but incapacity to grow.

Example 4

Secretion Capacities of the KBMA Strain Obtained in Example 3: OSTΔuvrAB Mutant is Inactivated by Photochemical Treatment, but Still Secrete Proteins As shown in FIG. 2C, the fusion protein ExoS54-OVA is detected in supernatant of P. aeruginosa photochemically treated with different level of amotosalen (0, 2, 5, 10, 15 and 20 µM). OSTΔuvrAB was transformed with plasmid pEAiS54 PADRE Ova. Resulting strains were grown in LB medium containing 300 mg/L carbenicillin (Cb) during the photochemical treatment. Cells were resuspended in LB 300 mg/L Cb with or without 5 mM EGTA and cultivated 3 hours at 37° C. The calcium depletion induced by EGTA triggers P. aeruginosa TTSS activation and secretion of TTSS effectors in culture medium {Epaulard, 2006 #25}. Supernatants were precipitated and analysed by SDS PAGE (Mini protean Tris Glycine 12% precast gel (Biorad)) and immunoblotting with polyclonal rabbit antibody anti chicken ovalbumin (AbDserotec) used at 1/5000 in TBS BSA 0.5 mg/mL to test the presence of secreted fusion protein ExoS54-PADRE Ova.

Figure 3:
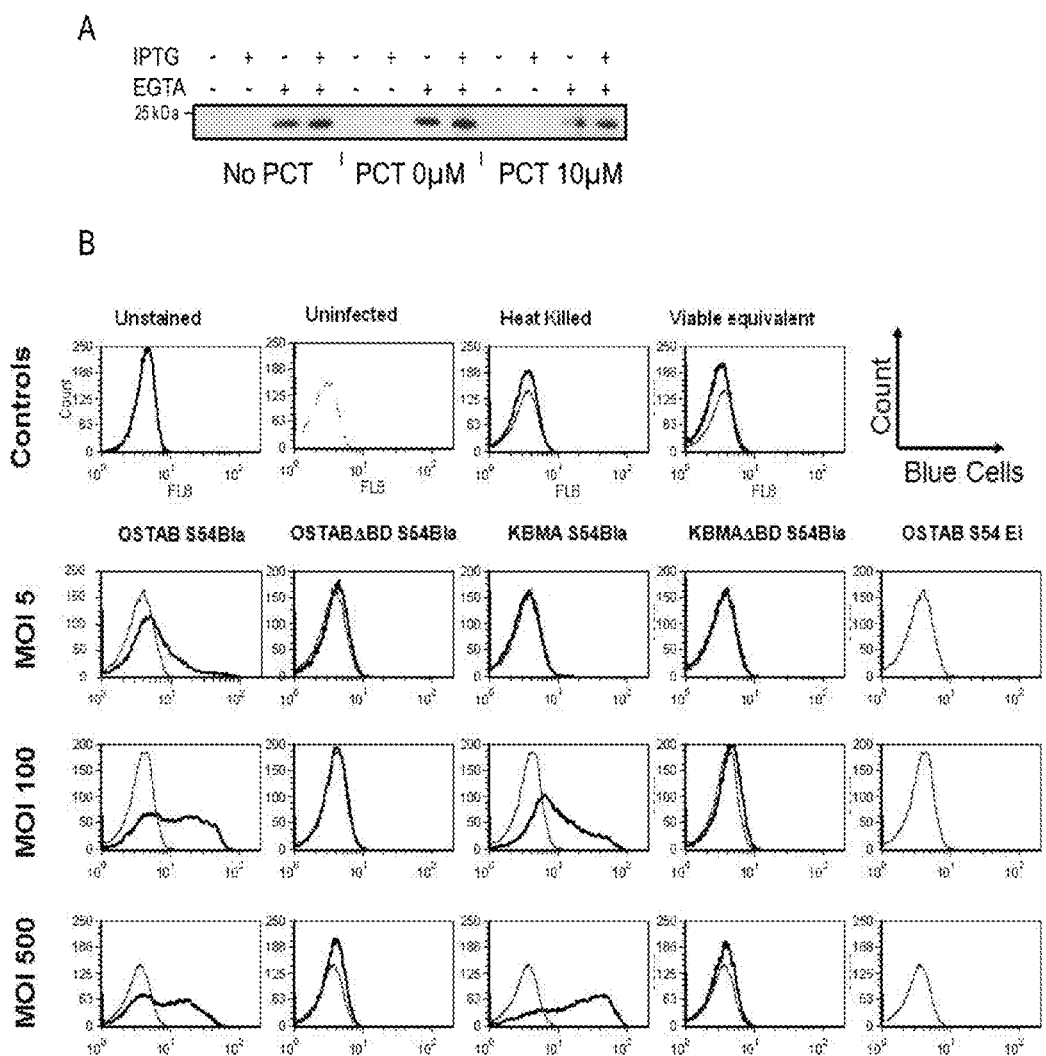
FIG. 3: A. KBMA *P. aeruginosa* photochemically treated with 10 µM amotosalen produces, secretes and inject antigen into dendritic cells. A. KBMA *P. aeruginosa* secrete ExoS54-Ovalbumin antigen into the supernatant. B. The type III secretion system of KBMA *P. aeruginosa* is functional. Injection of S54-Bla in human HL60 cells.

FIG. 2C shows that the antigen "PADRE Ova" is secreted as soon as EGTA is added in the culture medium, in any concentration of amotosalen. As shown in FIG. 3A, KBMA P. aeruginosa photochemically treated with 10 µM amotosalen secretes ExoS54-Ovalbumin antigen into the supernatant.

First, we obtained transformants of OSTΔuvrAB with plasmids pEAI S0-OVA (deleted for secretion Tag) and pEAi S54-OVA. We prepared photochemical treated strain in presence of psoralen (0 and 10 µM). Then, we assessed the production and secretion by TTSS of ExoS54-fused proteins by the PCT strains. After PCT, we used four growth conditions in LB medium: no TTSS stimulation, TTSS stimulation by calcium depletion (5 mM EGTA), OVA intrabacterial production without TTSS stimulation (0.5 mM IPTG) and supplementation with both EGTA and IPTG to test the production and secretion of OVA. As shown in FIG. 3B, the type III secretion system of KBMA P. aeruginosa is functional: the antigen S54-BIa is injected into cells.

To look further about the TTSS functionality of our KBMA strain, we used an assay measuring the cleavage of CCF2 in eukaryotic cell injected by β-lactamase fused to ExoS54. This test of the "effective injection of the antigen into cells" was previously described by Derouazi et al. {Derouazi, 2010 #203}. Briefly, after 3 h of infection of eukaryotic HL60 cells with various strains, cells were incubated with freshly prepared 6×CCF2/AM solution (1 µM final concentration; Invitrogen) for 30 min in the darkness at room temperature. The percentage of cells that received reporter fusions was quantified by flow cytometry (FACS Moflo; Dako Cytomation).

The five different tested strains are:
  OSTAB S54BIa: Strain of P. aeruginosa known to inject S54-BIa via TTSS
  OSTAB PopBD S54BIa: Strain of P. aeruginosa deleted for translocon PopBD unable to inject BIa via TTSS into cell
  KBMA S54BIa: KBMA expressing S54-bIa antigen
  KBMA PopBD S54BIa: KBMA strain deleted for translocon PopBD
  Heat killed: P. aeruginosa expressing S54-BIa heated at 70° C. for 1 hour
  Viable equivalent: Based on CFU graph, for KBMA at MOI 500 there is approximately 1 bacteria alived. This is 1 bacteria OSTAB S54 BIa.

The results are shown in FIG. 3B, and are expressed as number of cells that exhibit a blue fluorescence; uninfected cells incubated with CCF2 were used as negative control. FACS analysis revealed blue cells indicating CCF2-AM cleavage by BIa. No blue cells were observed in cells unstained, uninfected or infected with either equivalent viable bacteria (i.e. 1 bacteria equivalent for MOI 500) or strain harbouring empty plasmid (pEAi) or plasmid expressing wild type β-lactamase protein fused to S54 but not secreted via TTSS (OSTABΔpopBD S54-BIa) (FIG. 2B). Using KBMA strain, blue cells could be seen in HL60 infected at MOI 100 and 500 with increased yield, indicating that the TTSS is active under PCT. Together this data demonstrate that we obtain a KBMA P. aeruginosa at 10 µM S59-psoralen concentration, unable to replicate on nutrient agar medium but still able to secrete an antigen by its activated type III secretion system.

Example 5

Cytotoxicity of the Attenuated Strain Obtained in Example 3

The loss of cytotoxicity was assessed by infection of mouse dendritic cells (BMDCs). The PCT treated bacteria were prepared as mentioned above. Cytotoxicity was assessed by determination of lactate dehydrogenase release into supernatants of the infected cells using a cytotoxicity detection kit (LDH, Roche) as described previously {Dacheux, 1999 #81}. LDH release of infected cells was measured at 3 h post-infection. The percentage of cytotoxicity for each experiment was calculated with the following equation:

(Exp. value−control with only cells)/(control with Triton X-100 1%−control with only cells)×100. Data are the means of results of at least three experiments.

Figure 4:
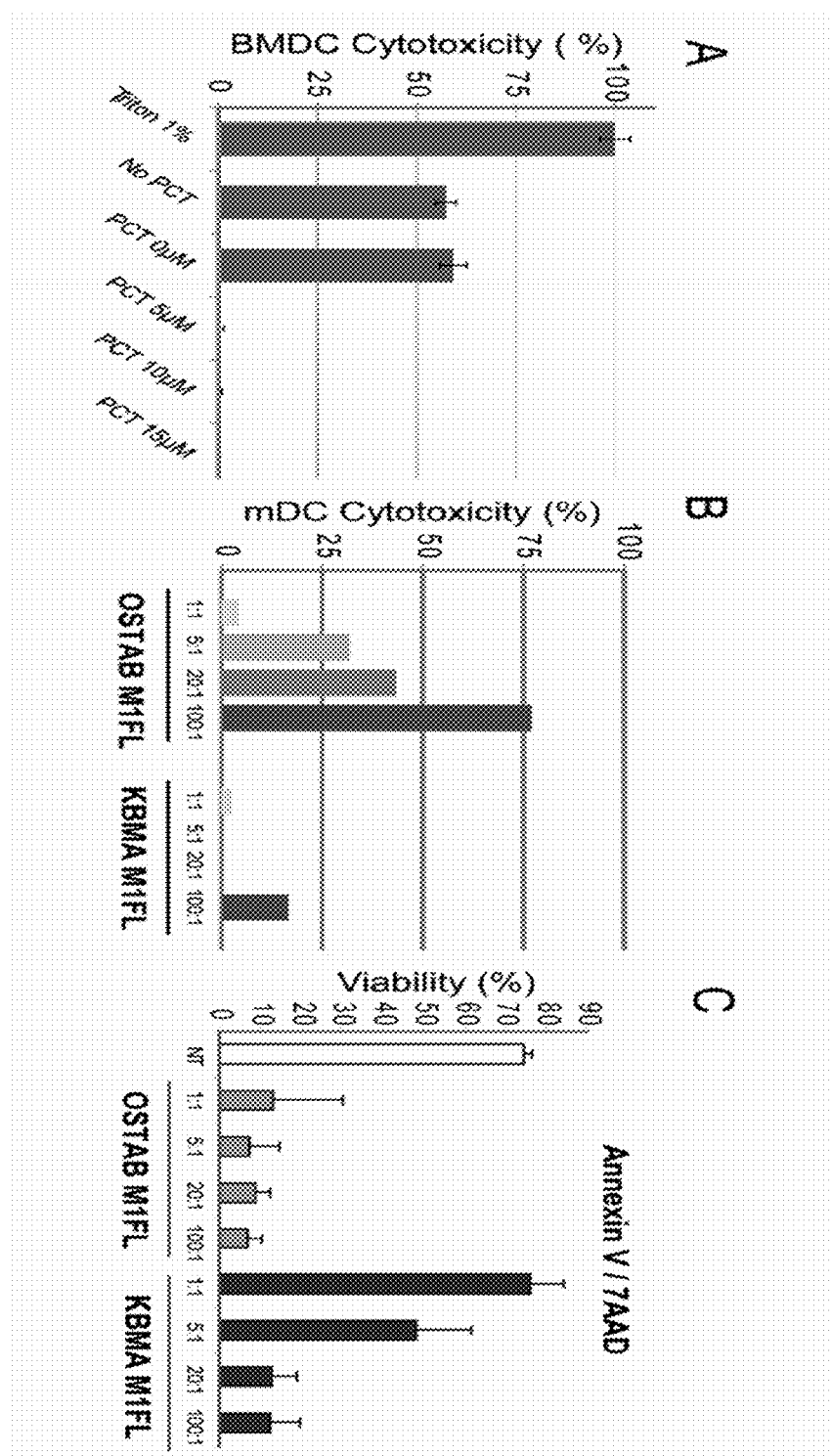
FIG. 4: KBMA *Pseudomonas aeruginosa* is less cytotoxic. A) Loss of cytotoxicity was assessed by infection of mouse dendritic cells (BMDCs). LDH release of infected cells was measured at 3 h post-infection. The percentages of cytotoxicity were calculated according to the release of LDH activity. Data are the means of results of at least three experiments. B) Cytotoxicity of KBMA *P. aeruginosa* (PCT 10 µM) to moDCs 3 h post infection. C) Effect of MOI on 7AAD/AnnexinV moDCs staining 24 h post infection. NT Control represents cells only.

Data are shown on FIG. 4A: photo-treated cells are not cytotoxic towards mouse dendritic cells. FIG. 4B shows the cytotoxicity on human dendritic cells. Tested strains are the following: OSTAB and KBMA expressing M1FIu Puerto Rico antigen (M1-K252) fused to ExoS54. FIG. 4C shows the viability of human moDCs 24 h post infection with KBMA or OSTAB S54-M1FI.

Example 6

Vaccination Protocol with the Adapted Strain Obtained in Example 1

Animal Experiments:

Female C57BL/6 mice were purchased from Janvier S A (Le Genest-Saint-Isle, France) and experimented at 6-8 weeks of age. They were kept under pathogen-free conditions in the animal facility of the University Joseph Fourier (Grenoble, France). All animal experiments were approved by the Animal Experiment Committee of the Region and were performed in accordance with institutional and national guidelines.

Animal Immunization:

A) Prophylactic assay: C57BL/6 mice were injected at four positions in right and left franks with CHA-CLIN1-PADRE-OVA strain at $5*10^7$ cells/position/time twice 14 days and 7 days before B16OVA tumor challenge. CHA-OST-EI is the negative control. Kaplan-Meyer curves displayed survival data from groups of 6 mice. Statistical analysis: $p<0.01$ for three immunized groups vs EI, no difference between immunized groups.

B) Therapeutic assay: C57BL/6 mice received a subcutaneously tumor challenge with GL261 tumor cells at day 0 and then were vaccinated with at four positions in right and left franks with CHA-CLIN1-PADRE-OVA strain at $5*10^7$ cells/position/time on following D1/D5/D9/D13/D17/D21 therapeutic schema. Kaplan-Meyer curves displayed survival data from groups of 6 mice. Statistical analysis: $p<0.01$ for three immunized groups vs EI; CHA-OST-PADRE-OVA vs CHA-CLIN1-PADRE-OVA 4 positions, $p=0.72$; CHA-OST-PADRE-OVA vs CHA-CLIN1-PADRE-OVA 1 position, $p=0.038$.

Tumor Challenge Experiment:

Immunized (prophylactic groups) or non-immunized (therapeutic groups) female C57BL/6 mice were injected subcutaneously in left flank on day 0 with B16-OVA cells at the dose of $2*10^8$ cells (100 µL)/mouse or GL261 cells at the dose of $1*10^8$ cells (100 µL)/mouse. The emergence and the dynamic growth of tumor mass were measured every 48 hours. When the diameter of tumor exceeded 10 mm, mice were sacrificed and this day corresponded to the period of survival. Analysis of data was realized with GraphPad Prism 5 software.

Statistical Analysis:

Bar graph analyses were evaluated by Student's t-test. Kaplan-Meyer survival curves of animals treated with different protocols were analyzed using the logrank test. A p-value below 0.05 between groups was considered to indicate a statistically significant difference.

Figure 5:
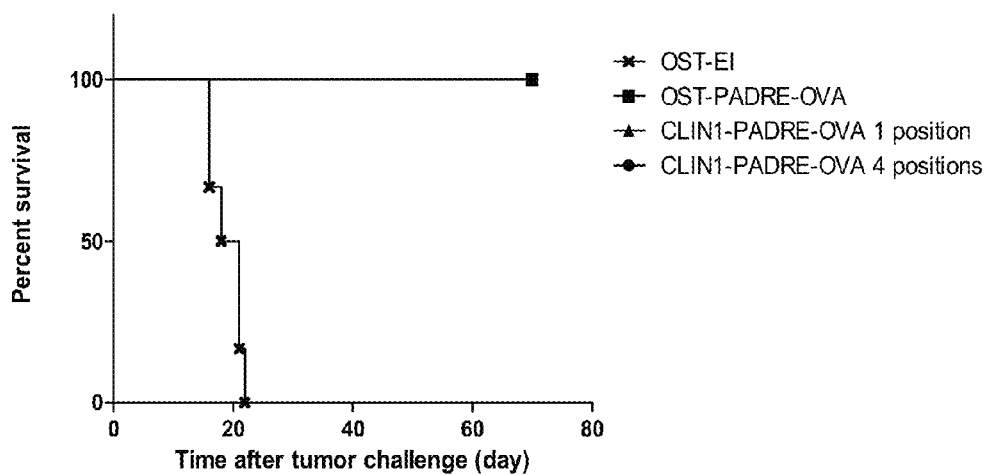
FIG. 5: Vaccination protocols. Evaluation of CHA-CLIN1 strain efficacy by tumor challenge on optimized vaccination protocol. (A) Prophylactic assay. (B) Therapeutic assay.
Figure 5:
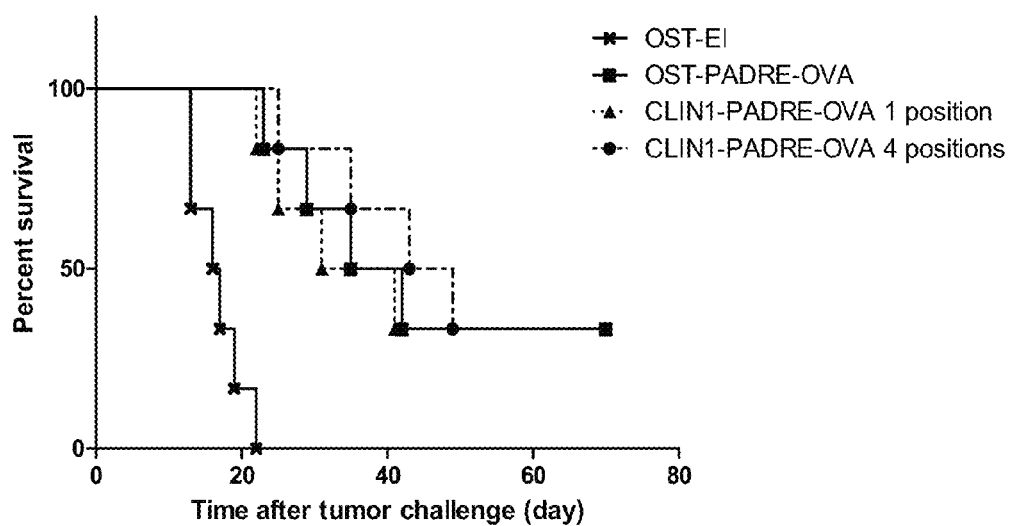

Results:

First of all, we found that $10^8$ CHA-CLIN1-PADRE-OVA/time primed the strongest CD8+ T response among the three doses, and we tried to optimize CHA-CLIN1 strain efficiency through a vaccination of mice at multi-positions (four subcutaneous injections in right and left flanks, $5*10^7$ bacteria/position/time, on D-14/D-7). CHA-CLIN1-PA-DRE-OVA vaccinations based on different protocols demonstrated the same efficacy as CHA-OST-PADRE-OVA strain (FIG. 5A).

For therapeutic assay, all immunized groups presented tumor rejections with slight differences between the three immunized group, CHA-CLIN1-PADRE-OVA vaccinations at four positions were slightly more efficient than CHA-OST-PADRE-OVA vaccinations which were still better than CHA-CLIN1-PADRE-OVA vaccinations at one position. It has to be noticed that no significant differences were found between CHA-OST-PADRE-OVA group and CHA-CLIN1-PADRE-OVA 4 position group, while the difference between CHA-OST-PADRE-OVA group and CHA-CLIN1-PADRE-OVA 1 position group was significant ($p=0.038$) (FIG. 5B).

CITED PATENT DOCUMENTS

EP 1 692 162 B1—Université Joseph Fourier

CITED NON-PATENT DOCUMENTS

Epaulard O, Toussaint B, Quenee L, Derouazi M, Bosco N, Villiers C, et al. *Anti-tumor immunotherapy via antigen delivery from a live attenuated genetically engineered Pseudomonas aeruginosa type III secretion system-based vector*. Mol Ther 2006 November; 14(5):656-61.

Epaulard O, Derouazi M, Margerit C, Marlu R, Filopon D, Polack B, et al. *Optimization of a type III secretion system-based Pseudomonas aeruginosa live vector for antigen delivery*. Clin Vaccine Immunol 2008 February; 15(2):308-13.

Brocksted D G, Bahjat K S, Giedlin M A, Liu W, Leong M, Luckett W, Gao Y, Schnupf P, Kapadia D, Castro G, Lim J Y, Sampson-Johannes A, Herskovits A A, Stassinopoulos A, Bouwer H G, Hearst J E, Portnoy D A, Cook D N, Dubensky T W Jr. *Killed but metabolically active microbes: a new vaccine paradigm for eliciting effector T-cell responses and protective immunity*. Nat Med. 2005 August; 11(8):853-60.

Wollowitz S. *Fundamentals of the psoralen-based Helinx technology for inactivation of infectious pathogens and leukocytes in platelets and plasma*. Semin Hematol. 2001 October; 38(4 Suppl 11):4-11.

DeBell R M. *Production of exotoxin A by Pseudomonas aeruginosa in a chemically defined medium*. Infect Immun 1979 April; 24(1):132-8.

Sambrook J, Russel D W. *Molecular Cloning, a laboratory manual, $3^{rd}$ edition*. Cold Spring Harbor Laboratory Press (2001).

Coligan, *Conventional immunological techniques are explained in Current protocol in Immunology*, John Wiley & Sons (2005).

Buonaguro L, Petrizzo A, Tornesello M L, Buonaguro F M. *Translating tumor antigens into cancer vaccines*. Clin Vaccine Immunol. 2011 January; 18(1):23-34. Review.

Novellino L, Castelli C, Parmiani G. *A listing of human tumor antigens recognized by T cells: March 2004 update*. Cancer Immunol Immunother. 2005 March; 54(3):187-207. Review.

Derouazi M, Wang Y, Marlu R, Epaulard O, Mayol J F, Pasqual N, Le Gouellec A, Polack B, Toussaint B. *Optimal epitope composition after antigen screening using a live bacterial delivery vector: application to TRP-2*. Bioeng Bugs. 2010 January-February; 1(1):51-60.

Dacheux D, Attree I, Schneider C, Toussaint B. *Cell death of human polymorphonuclear neutrophils induced by a Pseudomonas aeruginosa cystic fibrosis isolate requires a functional type III secretion system*. Infect Immun. 1999 November; 67(11):6164-7.

The invention claimed is:

1. An adapted strain of *Pseudomonas*, the adapted strain of *Pseudomonas* having deletions of ExoS, ExoT, aroA, and IasI genes and a doubling time when cultivated in a chemically defined medium comprising magnesium and calcium of less than 60 minutes, wherein the adapted strain of *Pseudomonas* has been deposited at the National Collection of Microorganisms Cultures (CNCM; Institut Pasteur) under the filing number I-4564.

2. A process for obtaining the adapted strain of *Pseudomonas* according to claim 1, comprising:
    deleting genes ExoS, ExoT, aroA and IasI in an initial *Pseudomonas* strain cultivated in a LB medium;
    progressively changing the culture medium from LB medium to a chemically defined medium comprising magnesium and calcium; and
    selecting the adapted strains presenting a doubling time inferior to 60 minutes when cultivated in the chemically defined medium.

3. The process according to claim 2, wherein the chemically defined medium has the following composition: a glucose minimal medium M9 supplemented with 1 mM $Mg^{2+}$ and 1 mM $Ca^{2+}$.

4. The process according to claim 2, wherein the adapted strain is furthermore treated to become 'killed but metabolically active'.

5. An immunogenic composition comprising the adapted strain of *Pseudomonas* according to claim 1.

6. A composition for inducing an immune response in a host, the composition comprising the adapted strain of *Pseudomonas* according to claim 1.

* * * * *

UNITED STATES PATENT AND TRADEMARK OFFICE
CERTIFICATE OF CORRECTION

PATENT NO. : 9,556,442 B2  
APPLICATION NO. : 14/364322  
DATED : January 31, 2017  
INVENTOR(S) : Audrey Le Gouellec et al.

Page 1 of 1

It is certified that error appears in the above-identified patent and that said Letters Patent is hereby corrected as shown below:

On the Title Page

Item (30), insert therefor:

-- (30)  Foreign Application Priority Data  
Dec. 12, 2011 (EP)..............................11306636.9 --

Signed and Sealed this
Twenty-eighth Day of March, 2017

Michelle K. Lee
*Director of the United States Patent and Trademark Office*